US011045575B2

(12) United States Patent
Koyama et al.

(10) Patent No.: US 11,045,575 B2
(45) Date of Patent: Jun. 29, 2021

(54) MATERIAL TO FORM A HYDROGEL

(71) Applicant: Yoshiyuki Koyama, Tokyo (JP)

(72) Inventors: Yoshiyuki Koyama, Tokyo (JP);
Tomoko Ito, Funabashi (JP)

(73) Assignee: Yoshiyuki Koyama, Tokyo (JP)

( * ) Notice: Subject to any disclaimer, the term of this patent is extended or adjusted under 35 U.S.C. 154(b) by 0 days.

(21) Appl. No.: 16/898,990

(22) Filed: Jun. 11, 2020

(65) Prior Publication Data

US 2020/0297894 A1 Sep. 24, 2020

Related U.S. Application Data

(60) Division of application No. 15/632,090, filed on Jun. 23, 2017, now Pat. No. 10,716,874, which is a continuation of application No. 14/693,098, filed on Apr. 22, 2015, now abandoned, which is a continuation of application No. PCT/JP2013/078612, filed on Oct. 22, 2013.

(30) Foreign Application Priority Data

Oct. 23, 2012 (JP) ................. 2012-233543
May 24, 2013 (JP) ................. 2013-109515

(51) Int. Cl.
*A61L 26/00* (2006.01)
*A61L 15/60* (2006.01)
*A61L 15/22* (2006.01)
*A61L 31/14* (2006.01)
*A61L 31/04* (2006.01)
*C08L 39/06* (2006.01)

(52) U.S. Cl.
CPC ............. *A61L 15/60* (2013.01); *A61L 15/225* (2013.01); *A61L 26/008* (2013.01); *A61L 26/009* (2013.01); *A61L 26/0014* (2013.01); *A61L 26/0023* (2013.01); *A61L 31/041* (2013.01); *A61L 31/145* (2013.01); *C08L 39/06* (2013.01); *A61L 2400/04* (2013.01)

(58) Field of Classification Search
CPC ..................................................... A61L 15/60
USPC ............................................................ 424/444
See application file for complete search history.

(56) References Cited

U.S. PATENT DOCUMENTS

| | | | |
|---|---|---|---|
| 5,578,661 A | 11/1996 | Fox | |
| 6,379,702 B1 | 4/2002 | Lorenz et al. | |
| 2002/0071855 A1 | 6/2002 | Sadozai | |
| 2005/0003012 A1 | 1/2005 | Woller et al. | |
| 2005/0196351 A1 | 9/2005 | Soshinsky | |
| 2010/0272669 A1 | 10/2010 | Malessa et al. | |
| 2011/0021964 A1 | 1/2011 | Larsen | |

FOREIGN PATENT DOCUMENTS

| | | |
|---|---|---|
| CN | 101267831 A | 9/2008 |
| JP | 60-215622 A | 10/1985 |
| JP | 4-054107 A | 2/1992 |
| JP | 5-155759 A | 6/1993 |
| JP | 6-040889 A | 2/1994 |
| JP | 6-040890 A | 2/1994 |
| JP | 2004-501956 A | 1/2004 |
| JP | 2007-526294 A | 9/2007 |
| JP | 2010-254688 A | 11/2010 |
| WO | WO 02/02079 A1 | 1/2002 |
| WO | WO 2005/092271 A1 | 10/2005 |
| WO | WO 2006-116524 A1 | 11/2006 |

OTHER PUBLICATIONS

Biswas et al. (Complexation and Blending of starch, poly(acrylic acid), and poly(N-vinyl pyrrolidone). (Year: 2006).*
Chen et al., "Fluorometric Study of the Equilibrium and Kinetics of Poly(Acrylic Acid) Association With Polyoxyethylene or Poly(Vinyl Pyrrolidone)", Eur. Polym. J., vol. 19, No. 10/11, 1983, pp. 923-928.
International Preliminary Report on Patentability and Written Opinion of the International Searching Authority (Forms PCT/IB/338, PCT/IB/373, PCT/ISA/237, and PCT/IB/326) for International Application No. PCT/JP2013/078612, dated May 7, 2015, with an English translation.
International Search Report issued in PCT/JP2013/078612, dated Jan. 21, 2014.
Ito et al., "Bioadhesive and Biodegradable Hydrogels as Antiadhesive and Hemostatic Materials", Abstracts of Symposium 2012 of the Japanese Society for Biomaterials, Sendai International Center, Nov. 26-27, 2012, p. 365.
Kirsh et al., "Chainlength Effects on Interactions of Polyvinylpyrrolidone With Low and High Molecular Compounds", European Polymer Journal, vol. 15, 1979, pp. 223-228.
Chinese Office Action dated Nov. 3, 2015, issued in corresponding Chinese Patent Application No. 2013800528393.
Chinese Office Action for Chinese Application No. 201380052839. 3, dated Jul. 13, 2016, with English translation.
Final Office Action issued in copending U.S. Appl. No. 14/693,098 dated Mar. 23, 2017.
Final Office Action issued in copending U.S. Appl. No. 15/632,090 dated Dec. 2, 2019.
Ito et al. "Bioabsorbable bioadhesive hydrogel comprising poly(acrylic acid) and poly (vinylpyrrolidone) for adhesion barrier and hemostatic device." MRS Communications, vol. 5, Issue 2, 2015, pp. 291-295.
Japanese Office Action, dated Feb. 28, 2017, for Japanese Application No. 2013-109515, as well as a Concise Explanation of the Office Action.

(Continued)

*Primary Examiner* — Sarah Alawadi
(74) *Attorney, Agent, or Firm* — Birch, Stewart, Kolasch & Birch, LLP

(57) ABSTRACT

A soft film, a sponge, or a sheet in the dried state is provided, which is capable of forming a hydrogel absorbing water or blood. The film is obtainable by preparing a film-state material in the dried state from either a solution of poly (acrylic acid) or a solution of polyvinylpyrrolidone, and bringing the film-state material into contact with the other remaining solution, and then drying or freeze-drying it.

9 Claims, No Drawings

(56) References Cited

OTHER PUBLICATIONS

Kaczmarek et al. "Study of poly(acrylic acid)-poly(vinylpyrrolidone) complexes and their photostability." 2001.
Kadlubowski et al., "Hydrogels of polyvinylpyrrolidone (PVP) and poly(acrylic acid) (PAA) synthesized by radiation-induced crosslinking of homopolymers." 2009.
Non-Final Office Action issued in copending U.S. Appl. No. 14/693,098 dated Sep. 8, 2016.
Non-Final Office Action issued in copending U.S. Appl. No. 15/632,090 dated May 17, 2019.
Notice of Allowance issued in copending U.S. Appl. No. 15/632,090 dated Mar. 20, 2020.
Pradip et al., Polymer—Polymer Complexation in Dilute Aqueous Solutions: Poly(acrylic acid)-Poly(ethylene oxide) and Poly(acrylic acid)-Poly(vinylpyrrolidone), Langmuir, vol. 7, No. 10 (1991) pp. 2108-2111.
Restriction Election Requirement issued in copending U.S. Appl. No. 14/693,098 dated Apr. 15, 2016.
Restriction Election Requirement issued in copending U.S. Appl. No. 15/632,090 dated Mar. 1, 2019.
Taiwanese Office Action, dated Dec. 1, 2016, for Taiwanese Application No. 102138257, with an English translation.

\* cited by examiner

MATERIAL TO FORM A HYDROGEL

CROSS-REFERENCE TO RELATED APPLICATIONS

This application is a Divisional of copending U.S. application Ser. No. 15/632,090, filed on Jun. 23, 2017, which is a Continuation of U.S. application Ser. No. 14/693,098, filed on Apr. 22, 2015, which is a Continuation application from International Patent Application No. PCT/JP2013/078612, filed Oct. 22, 2013, claiming the benefit of the conventional priority from Japanese Patent Application No. 2012-233453, filed Oct. 23, 2012; and Japanese Patent Application No. 2013-109515, filed May 24, 2013, all of which are hereby expressly incorporated by reference into the present application.

BACKGROUND OF THE INVENTION

1. Field of the Invention

The present invention relates to a film or sponge which can be utilized for an adhesion barrier or hemostatic device.

Specifically, the present invention relates to a film or sponge which can be provided as a soft film or sponge in the dried state, and can form a hydrogel absorbing water or blood.

2. Background Art

A hydrogel which can adhere to a bio-tissue has been widely explored to be applied to an adhesion barrier, hemostatic device, wound covering material, or drug-release device, and some are practicalized. A film or sponge which can adhere to wet bio-tissues such as mucous membrane or serous membrane to form an adhesive gel absorbing water around is useful as an adhesion barrier or hemostatic device Hydrogels derived from animal protein is known, but they have the risk of infection of viruses or bovine spongiform encephalopathy, or immune response to foreign proteins. To avoid such risks, crosslinked natural polysaccharides were also developed. However, crosslinked natural polysaccharides are not very flexible in the dried state, difficult in fitting to a complex shape, and thus, have a difficulty in using as an adhesion barrier. There is a problem that the chemically crosslinked gel is hard to be bio-absorbed. Recently, reports about the hydrogel comprising synthetic polymers are increasing. However, the biocompatibility of the gels of synthetic polymers is low, and there is a problem that the preparation of them is generally complicated.

A hydrogel formed by synthetic polymers, poly(acrylic acid) and polyvinylpyrrolidone, through hydrogen bonding is known (Eur. Polym. J., 15, 223, 1979; Eur. Polym. J., 19, 923, 1983). This hydrogel has biocompatibility, and easy to be prepared. Therefore, it is expected as a hydrogel which avoids the problems above. The hydrogel of poly(acrylic acid) and polyvinylpyrrolidone is formed immediately by mixing of their aqueous solutions, but it precipitates soon forming fibrous aggregates through hydrogen bonding. Therefore, there is a problem that the film or sponge to form hydrogel cannot be prepared by merely mixing the aqueous solutions. A hard solid can be obtained by isolating and drying the aggregate. However, if the aggregate is rehydrated, it does not absorb water and remains as a solid, and a hydrogel cannot be reproduced.

On the other hand, it was proposed to utilize the mixture of poly(acrylic acid) and polyvinylpyrrolidone as a material for slow release device (Example 1 in Japanese Patent Application Laid-open No. Sho 60-215622, and others). Slow release formulation to be a soft gel by absorbing water, which was improved for its drug slow release behavior by addition of cyclodextrin to the mixture of poly(acrylic acid) and polyvinylpyrrolidone, was proposed (Japanese Patent Application Laid-open No. Hei 06-40890). The suppository preparation containing poly(acrylic acid) and polyvinylpyrrolidone was also proposed (Japanese Patent Application Laid-open No. Hei 06-40889). However, these technologies are not for utilizing the hydrogel comprising poly(acrylic acid) and polyvinylpyrrolidone as a material or treatment material for medical use. Thus, in those publications, no indication nor instruction for the technology to reproduce the hydrogel by rehydration of the isolated and dried gel is found.

PRIOR ART DOCUMENTS

Patent Documents

Patent Document 1: Japanese Patent Application Laid-open No. Sho 60-215622
Patent Document 2: Japanese Patent Application Laid-open No. Hei 06-40890
Patent Document 3: Japanese Patent Application Laid-open No. Hei 06-40889

Non-Patent Documents

Non-Patent Document 1: Eur. Polym. J., 15, 223, 1979
Non-Patent Document 2: Eur. Polym. J., 19, 923, 1983

SUMMARY OF THE INVENTION

1. Problems to be Solved by the Invention

The present invention has as an object to provide a film or sponge which can be utilized for an adhesion barrier or hemostatic device.

Specifically, the present invention has as an object to provide a film or sponge which can be provided as a soft film or sponge in the dried state, and can form a hydrogel absorbing water or blood.

2. Means for Solving the Problems

As mentioned above, when the aqueous solutions of poly(acrylic acid) and polyvinylpyrrolidone are mixed, the hydrogel is formed immediately by hydrogen bonding of poly(acrylic acid) and polyvinylpyrrolidone. However, there is a problem that it precipitates soon forming fibrous aggregates through hydrophobic bonding. In addition, there is a problem that hydrogel cannot be effectively reproduced by hydrating the aggregate which was isolated and dried.

The inventors of the present invention conducted extensive studies on the biocompatible hydrogel obtainable from poly(acrylic acid) and polyvinylpyrrolidone so that the hydrogel can be easily utilized as an adhesion barrier or hemostatic device. Especially, the inventors of the present invention intensively investigated to provide means to prepare a soft dried gel by drying the hydrogel obtained from poly(acrylic acid) and polyvinylpyrrolidone, and those to prepare the adequately hydrated hydrogel absorbing water by hydrating the gel in the dried state.

Finally, the inventors found that a soft film could be obtained by drying either an aqueous solution of poly (acrylic acid) or that of polyvinylpyrrolidone so as to form a film, followed by bringing the film into contact with the solution of the other polymer, and then drying it. They also found that the film formed a hydrogel absorbing water. The inventors also found that when the film in the dried state was put on a tissue surface or a bleeding site, it absorbed water or blood rapidly to form a gel, which was very effective in avoiding adhesion or arresting hemorrhage. Moreover, they confirmed that the hydrogel produced from the attached film was slowly degraded and solubilized under physiological conditions after being attached.

The inventors of the present invention found that the soft elastic spongy solid which is obtainable by freeze-drying a mixed solution of poly(acrylic acid) and polyvinylpyrrolidone under the presence of a water-soluble polymer such as hyaluronic acid or a salt thereof could be utilized as the film mentioned above. Moreover, they found that a sheet like Japanese paper could be obtained by drying either an aqueous solution of poly(acrylic acid) or an aqueous solution of polyvinylpyrrolidone so as to form a film, followed by bringing the film into contact with a solution of the other solution, and then freeze-drying it, and be utilized as the film or sponge mentioned above. Moreover, they found that a powder being obtained by crushing the breakable solid which is obtainable by freeze-drying a mixed solution of poly(acrylic acid) and polyvinylpyrrolidone under the presence of a water-soluble polymer, and a powder which is obtainable by spray drying the solutions of poly(acrylic acid) and polyvinylpyrrolidone on mixing could be utilized as the film or sponge mentioned above as a material to form a hydrogel. The present invention was achieved based on those findings.

Namely, the present invention provides a film to form a hydrogel, comprising poly(acrylic acid) and polyvinylpyrrolidone, wherein the film is obtainable by preparing a film-state material in the dried state from either a solution of poly(acrylic acid) or a solution of polyvinylpyrrolidone, and bringing the film-state material into contact with the other remaining solution, followed by being dried.

The invention mentioned above provides preferable embodiments such as: the film mentioned above which is obtainable by preparing the film-state material from the solution of poly(acrylic acid), and bringing the film-state material into contact with the solution of polyvinylpyrrolidone, followed by being dried; the film mentioned above which is obtainable by bringing the film-state material including either poly(acrylic acid) or polyvinylpyrrolidone into contact with the solution of the other remaining polymer by dropwise addition or spraying, followed by being dried; the film mentioned above wherein the solution(s) of poly(acrylic acid) and/or polyvinylpyrrolidone include(s) poly(vinyl alcohol); and the film mentioned above wherein the solutions are aqueous solutions or of organic solvents, or mixed solutions of water and organic solvents.

Moreover, the present invention provides a method for producing a film including poly(acrylic acid) and polyvinylpyrrolidone to form a hydrogel, the method comprising the steps of: preparing a film-state material in the dried state from either a solution of poly(acrylic acid) or a solution of polyvinylpyrrolidone; and bringing the film-state material into contact with the other remaining solution, followed by being dried.

From another aspect, the present invention provides a sponge to form a hydrogel, comprising poly(acrylic acid) and polyvinylpyrrolidone, wherein the sponge is obtainable by freeze-drying a mixed solution of poly(acrylic acid) and polyvinylpyrrolidone under the presence of a water-soluble polymer.

The invention mentioned above provides preferable embodiments: the sponge mentioned above, wherein the water-soluble polymer is selected from polysaccharides or synthetic water-soluble polymers; the sponge mentioned above, wherein the water-soluble polymer is mucopolysaccharides; and the sponge mentioned above, wherein the water-soluble polymer is hyaluronic acid or a salt thereof. In addition, the sponge which is obtainable by freeze-drying the solution being obtained by mixing the solution of poly(acrylic acid) and the solution of polyvinylpyrrolidone under the presence of hyaluronic acid, is provided. As a solution, an aqueous solution is preferable.

A method for producing a sponge including poly(acrylic acid) and polyvinylpyrrolidone to form a hydrogel is provided, the method comprising a step of freeze-drying a mixed solution of poly(acrylic acid) and polyvinylpyrrolidone under the presence of a water-soluble polymer.

From another aspect, the present invention provides a papyraceous sheet to form a hydrogel, comprising poly(acrylic acid) and polyvinylpyrrolidone, wherein the sheet is obtainable by preparing a film-state material in the dried state from either a solution of poly(acrylic acid) or a solution of polyvinylpyrrolidone, and bringing the film-state material into contact with a solution including the other remaining polymer and a water-soluble polymer, followed by being frozen and then being freeze-dried.

The invention mentioned above provides a preferable embodiment: the papyraceous sheet mentioned above which is obtainable by preparing the film-state material in the dried state from the solution of poly(acrylic acid), and bringing the film-state material into contact with a solution including polyvinylpyrrolidone and hyaluronic acid, followed by being frozen and then being freeze-dried.

Moreover, the present invention provides a method for producing a papyraceous sheet including poly(acrylic acid) and polyvinylpyrrolidone to form a hydrogel, the method comprising the steps of: preparing a film-state material in the dried state from either a solution of poly(acrylic acid) or a solution of polyvinylpyrrolidone; and bringing the film-state material into contact with a solution of the other polymer and a water-soluble polymer, followed by being frozen and then being freeze-dried.

Moreover, the present invention provides a powder to form a hydrogel, comprising poly(acrylic acid) and polyvinylpyrrolidone, wherein the powder is obtainable by drying a droplet of solutions of poly(acrylic acid) and polyvinylpyrrolidone. Preferably, the powder mentioned above is obtainable by spray-drying the solution mentioned above. In addition, the powder to form a hydrogel, comprising poly(acrylic acid) and polyvinylpyrrolidone, wherein the powder is obtainable by crushing a breakable solid which is obtainable by freeze-drying the mixed solution of poly(acrylic acid) and polyvinylpyrrolidone under the presence of a water-soluble polymer, is provided.

From another aspects, medical treatment materials comprising the film, sponge, papyraceous sheet, and powder mentioned above are provided. Examples of the medical treatment materials may include an adhesion barrier, hemostatic device, and wound covering material.

3. Effects of the Invention

According to the present invention, a film, sponge, papyraceous sheet, and powder containing poly(acrylic acid) and polyvinylpyrrolidone, to form a hydrogel, are provided.

Those film, sponge, and papyraceous sheet have adequate flexibility and can be applied to a tissue surface or bleeding site in the tightly adhered state. They form a hydrogel absorbing water or blood, and strongly adhere to the application site to achieve treatment for avoiding adhesion or arresting hemorrhage. The powder mentioned above can also strongly adhere to the application site to achieve treatment for arresting hemorrhage. Both poly(acrylic acid) and polyvinylpyrrolidone are safe synthetic polymers approved as pharmaceutical excipients, and are highly biocompatible safe materials. Therefore, the film, sponge, papyraceous sheet, and powder of the present invention can be safely used as a medical treatment material. The hydrogel formed is slowly degraded and solubilized under physiological conditions after being applied, so it is safe to place it in a body as an adhesion barrier.

DETAILED DESCRIPTION OF THE PREFERRED EMBODIMENTS

A film provided by the present invention is characterized in that the film is to form a hydrogel, contains poly(acrylic acid) and polyvinylpyrrolidone, and is obtainable by preparing a film-state material in the dried state from either a solution of poly(acrylic acid) or a solution of polyvinylpyrrolidone, and bringing the film-state material in the dried state into contact with a solution of the other remaining solution, and then drying it.

The molecular weight of poly(acrylic acid) is not especially limited, but it is able to use those having a number average molecular weight of about 1,000 to 10,000,000, or crosslinked ones in the high molecular weight gel state. The molecular weight of polyvinylpyrrolidone is not especially limited, but it is able to use those having a number average molecular weight of about 1,000 to 10,000,000. Sodium salts of poly(acrylic acid) can be used as poly(acrylic acid) in some cases.

As a solvent to dissolve poly(acrylic acid) and polyvinylpyrrolidone, it is able to use water, organic solvents such as methanol, ethanol, and acetone, which can be mixed with water at any ratio, or organic solvents. Preferably, it is able to use water, ethanol, or the mixture of water and ethanol, but not limited to those.

To prepare the film provided by the present invention, first, a film-state material is prepared from either the solution of poly(acrylic acid) or polyvinylpyrrolidone in the dried state. The concentration of the solution is not especially limited, but it is able to use those of about 0.01% to 10%, preferably about 0.1% to 1%.

The method to prepare the solid film from the solution of poly(acrylic acid) or polyvinylpyrrolidone is not especially limited, but it can be prepared by, for example, putting the solution of poly(acrylic acid) or polyvinylpyrrolidone on a plate and extending it uniformly, and removing the solvent by air-blowing or heating. The depth of the solution on the plate is not especially limited, but it can be selected between about 1 μm and 50 mm.

The thickness of the film-state material after drying is not especially limited, but it is, generally, between about 0.1 μm and 5 mm. Drying can be carried out, for example, under heating at about 50-100° C., and sometimes it is favorable to be performed under lower temperature with air-blowing or reducing pressure. A water content of the film-state material after drying is not especially limited, but it is, generally, between about 0.1% and 10%.

The film provided by the present invention is obtainable by the dried film-state material containing either poly (acrylic acid) or polyvinylpyrrolidone into contact with the solution of the other remaining solution, and then drying it. The concentration of the latter solution of poly(acrylic acid) or polyvinylpyrrolidone used for contacting is not especially limited, but it is able to use those of about 0.01% to 10%, preferably about 0.1% to 1%.

The methods for bringing the dried film-state material into contact with the solution contining either poly(acrylic acid) or polyvinylpyrrolidone are not especially limited. For example, the methods such as dropwise addition, coating, or spraying of the solution can be enumerated, but are not limited to those. The amount of the solution of poly(acrylic acid) or polyvinylpyrrolidone to be used for contacting to the dried film-state material is not especially limited; however, in some cases, it is preferable to adjust the concentration and amount of the solution so that the ratio of the repeating mole unit of the poly(acrylic acid) or polyvinylpyrrolidone included in the dried film-state material to the repeating mole unit of poly(acrylic acid) or polyvinylpyrrolidone in the solution to be used for contacting is 0.1 to 10, preferably 0.5 to 2.

Drying of the film-state material after contacting with the solution mentioned above can be carried out, for example, under heating at 50-100° C., and sometimes lower temperature is favorable to be performed with air-blowing or reducing pressure. In the present specification, the term of "drying" must be interpreted most widely; thus, this term means not only as a state with completely removal of water but also as the state still containing some water in the way of drying process, and this term must not be interpreted limitedly as any meanings. The water content of the film provided by the present invention after drying is not especially limited, but it is, for example, between about 0.1% and 10%. The thickness of the film provided by the present invention after drying is not especially limited, but it is, for example, between about 0.1 μm and 1 mm.

It is possible to add poly(vinyl alcohol) to the solution to prepare the film-state material and/or the solution to contact with the film-state material, and it is preferable embodiments in the present invention for preparing the film being superior in strength. The amount of poly(vinyl alcohol) to be added is not especially limited, but, for example, the ratio of the repeating mole unit of poly(vinyl alcohol) to the repeating mole unit of poly(acrylic acid) can be about 0.01 to 50, preferably 0.1 to 10.

In some cases, it is favorable to add poly(vinyl alcohol) to the solution to contact with the film-state material. For example, in some cases, it is favorable to prepare the film at the molar ratio of poly(acrylic acid) to polyvinylpyrrolidone about 1:1 in repeating unit, using poly(vinyl alcohol) at the repeating unit molar ratio of about 5 to 20. It is favorable to add poly(ethylene glycol) to the solutions mentioned above. In some cases, by adding poly(ethylene glycol), flexibility of the film increases, and the rates of absorbing water and swelling are improved. As poly(ethylene glycol), for example, poly(ethylene glycol) 400 or poly(ethylene glycol) 4000 can be used, but it is not limited to those.

A sponge of the present invention is characterized in that the sponge is to form a hydrogel, contains poly(acrylic acid) and polyvinylpyrrolidone, and is obtainable by freeze-drying the mixed solution of poly(acrylic acid) and polyvinylpyrrolidone under the presence of a water-soluble polymer. The sponge provided by the present invention has flexibility, and also elasticity owing to the air involved in the solid structure.

As a solvent to dissolve poly(acrylic acid) and polyvinylpyrrolidone, it is able to use water, the organic solvents such as methanol, ethanol, acetone, which can be mixed with water at any ratio, or organic solvents. It is preferable to use only water for efficient freeze-drying.

As a water-soluble polymer, water-soluble polymers other than poly(acrylic acid) and polyvinylpyrrolidone such as polysaccharides or synthetic water-soluble polymers can be used. Preferably, water-soluble polymers which can be utilized as thickener can be used. For example, as polysaccharides, the followings can be enumerated; cellulose derivatives such as hydroxyethyl cellulose, carboxymethyl cellulose, hydroxypropyl methylcellulose, mucopolysaccharides such as hyaluronic acid, chondroitin sulfate, and natural water-soluble polysaccharides such as carrageenan, pectin, Locust bean gum, gum guaiac, xanthan gum, Whelan, but it is not limited to those. As a synthetic water-soluble polymer, it is able to use poly(vinyl alcohol) and others. As a water-soluble polymer, it is preferable to use hyaluronic acid and its salts. As hyaluronic acid and its salts, for example, it is preferable to use hyaluronic acid sodium salts and others. The molecular weight of hyaluronic acid is not especially limited, but it is, in some cases, preferable to use, for example, those having a number average molecular weight of not less than 200,000. By increasing the content of hyaluronic acid, in some cases, strength of the sponge increases, and tough sponge can be prepared.

The sponge of the present invention is obtainable by preparing the solution by mixing poly(acrylic acid) and polyvinylpyrrolidone under the presence of a water-soluble polymer, preferably hyaluronic acid or its salts, followed by freeze-drying the solution. Generally, the solution can be prepared as follows: the solution of poly(acrylic acid) or polyvinylpyrrolidone is prepared; then, water-soluble polymer, preferably hyaluronic acid or its salts, is added; and finally, the solution of the other polymer is added. However, the method to prepare the solution to be freeze-dried is not limited to this. Mixing of the solution can be carried out at 0° C. to room temperature. Freeze-drying can be performed by conventional method. If the solution is frozen in the mold and then freeze-dried, the sponge with a desired shape can be obtained. The water content after freeze-drying is not especially limited, but it is, for example, between about 0.1% and 10%. The density of the sponge of the present invention after freeze-drying is not especially limited, but it is, for example, between about 0.01 g/cm$^3$-0.9 g/cm$^3$.

The concentration of poly(acrylic acid) and polyvinylpyrrolidone in the solution to be freeze-dried is not especially limited. It can be, for example, about 0.01% to 1%. The molar ratio of the repeating unit of poly(acrylic acid) to the repeating unit of polyvinylpyrrolidone in the solution can be about 0.1 to 10, preferably 0.5 to 2. The amount of hyaluronic acid or its salts, to be added is at the ratio of the repeating mole unit of hyaluronic acid to the repeating mole unit of poly(acrylic acid) or polyvinylpyrrolidone can be about 0.01 to 50, preferably 0.1 to 10. It is preferable to add hyaluronic acid or its salts as, for example, an aqueous solution. For example, in some cases, it is favorable to prepare the sponge at the molar ratio of poly(acrylic acid) to polyvinylpyrrolidone about 1:1 in repeating unit, using water-soluble polymer, preferably hyaluronic acid sodium salt, at the repeating unit molar ratio of about 0.1 to 0.2.

Water-soluble polymer, preferably poly(vinyl alcohol), can be added to one or both of the solutions of poly(acrylic acid) or polyvinylpyrrolidone. If polysaccharide is used as a water-soluble polymer, water-soluble polymer, preferably poly(vinyl alcohol), can be added to the solutions of polysaccharide. Under this condition, the amount of water-soluble polymer, preferably poly(vinyl alcohol), is not especially limited. It is, for example, at the ratio of the repeating mole unit of poly(vinyl alcohol) to the repeating mole unit of poly(acrylic acid) can be about 0.01 to 50, preferably 0.1 to 10.

A papyraceous sheet provided by the present invention is characterized in that the papyraceous sheet to form a hydrogel, contains poly(acrylic acid) and polyvinylpyrrolidone, and is obtainable by preparing a film-state material from either a solution of poly(acrylic acid) or a solution of polyvinylpyrrolidone, and bringing the film-state material into contact with the solution including the other polymer and a water soluble polymer, followed by frozen and then being freeze-dried. In the present specification, the term of "papyraceous" means a state in which fibrous polymer gathers like a paper, having much space, and, preferably, forming an elastic solid including air. Preferably the term means a state like Japanese paper produced in Japan. This term must not be interpreted limitedly as any meanings and must be interpreted most widely.

In the embodiment mentioned above, as a means to prepare the film-state material in the dried state from either a solution of poly(acrylic acid) or a solution of polyvinylpyrrolidone, an appropriate means mentioned above can be selected. Generally, it is favorable to prepare the film-state material from the solution of poly(acrylic acid). A means for bringing the film-state material into contact with the solution including the other remaining polymer and a water-soluble polymer can be properly selected from the common methods such as dropwise addition, coating, or spraying. As a water-soluble polymer, the material mentioned above can be used, and preferably hyaluronic acid can be used. It is favorable to contact the solution with the film-state material to form a uniform thin layer on its surface.

The papyraceous sheet of the present invention is prepared by freezing and then freeze-drying the film-state material that has been contacted with the solution. From the point for efficient freezing and freeze-drying, the solutions mentioned above, preferably, are aqueous solutions. Freezing can be carried out, for example, at −20° C., but it is not limited to this temperatuare. The ratio of poly(acrylic acid), polyvinylpyrrolidone, and water-soluble polymer can be appropriately selected using the ratios mentioned above as reference.

A powder provided by the present invention is characterized in that the powder is to form hydrogel, contains poly(acrylic acid) and polyvinylpyrrolidone, and is obtainable by drying the solution of poly(acrylic acid) or polyvinylpyrrolidone as a droplet soon after the mixing. The powder of this embodiment is obtainable by, for example, spray drying the solution mentioned above by a spray drier equipped with an appropriate nozzle. Water-soluble polymer can be added to the solution as needed.

A powder of the another aspect is provided, the powder being to form a hydrogel, containing poly(acrylic acid) and polyvinylpyrrolidone, and being obtained by crushing a breakable solid obtainable by freeze-drying a mixed solution of poly(acrylic acid) and polyvinylpyrrolidone under the presence of water-soluble polymer. To produce the powder, the breakable solid can be prepared by the methods mentioned above. Crushing can be performed easily by appropriate a physically powerful effect. The size of the powder in the situations above is not especially limited, and can be selected as needed between several μm and several mm.

The intended use of the film, sponge, papyraceous sheet, and powder provided by the present invention is not especially limited, and can be used as, for example, a medical treatment material. They can be suitably used as, for example, an adhesion barrier for internal organs for a surgical operation, hemostatic device for a surgical operation or injury, or a wound covering material as protecting or healing acceleration.

A wound is, generally, a damage with failure of the skin, and as example, cut wound, laceration, chop wound, abrasion, crush injury, contusion; bruise, bullet wound, injuries caused by bombing, sting, impalement injury, or biting wound, and also burn or bedsore are anumerated, but it is not limited to these. It can be applied to a light wound without failure of the skin. The film, sponge, papyraceous sheet, and powder provided by the present invention can be used as a covering material for these wounds, and simultaneously as a hemostatic device for bleeding from wound site, and also as an absorber for lymph fluid from the wound site.

Adhesion is a phenomena where the tissues or organs normally separated are connected, and scar tissue is formed. It occurs, for example, after a surgical operation in the fields of gastrointestinal division, cardiology, plastic surgery, gynecology, or ophthalmology. It occurs as adhesion between gut walls, or between gut wall and abdominal wall in cases of inflammatory bowel disease. As an adhesion of internal organs, other than the adhesion occurring after a surgical operation, inflammatory bowel disease, irritable bowel syndrome, a duodenal ulcer, acute enteritis, protein-losing enteropathy, colorectal cancer, appendicitis, hemorrhagic colitis, intestinal tuberculosis, intestinal Behcet, adhesive intestinal obstruction (intestinal blockage) by diverticulosis of colon, adhesion in the abdominal cavity by peritoneal dialysis, or uterine synechia by Asherman's syndrome are enumerated, but it is not limited to these. As an adhesion barrier film, an adhesion barrier film consisting of polysaccharides (such as hyaluronic acid) (brand name: Seprafilm) was practicalized, and the film and sponge provided by the present invention can be used as an adhesion barrier as the products above.

The film, sponge, papyraceous sheet, and powder provided by the present invention can be mixed with one or more agents such as, for example, antibiotics, antiinflammatory agent, a blood coagulating agent, an anticoagulant, a local anesthetic, a vasoconstrictor or vasodilatation agent. For example, when the film, sponge, papyraceous sheet, or powder provided by the present invention is used as an adhesion barrier in the abdominal operation, it can be mixed with agents such as antibiotics, a blood coagulating agent, and/or antiinflammatory agent. For example, when the film, sponge, papyraceous sheet, or powder provided by the present invention is used as a hemostatic agent, it can be mixed with agents such as antibiotics, and also with local anesthetics as needed.

The film, sponge, papyraceous sheet, and powder provided by the present invention are provided as in a dried state. They can be provided as being retained on a support, or a film including a support, as needed. Especially, the film, sponge, papyraceous sheet, and powder provided by the present invention can be preferably provided also as being retained on a support, or a film including a support such as, for example, cloth or nonwoven fabrics of cotton or the staple fiber, a film or foam seat of soft poly(vinyl chloride), polyethylene or polyurethane, or a gauze. The powder of the present invention can be adhered to gauze or something. The film, sponge, papyraceous sheet, and powder provided by the present invention are preferably provided as a sterile conditions, and are preferably stored in a container in a sealed condition after being sterilized by common methods such as gas sterilization.

EXAMPLE

The following provides a more detailed explanation of the present invention through examples; however, the scope of the present invention cannot be limited by the examples in any way.

Example 1

Following materials were used in the experiments.

Poly(acrylic acid) (PAA): Carbopol (registered trademark) 940, 934Lubrizol Advanced Materials Inc.; or Carbopol 934P NF Polymer, Kobayashi Perfumery Co., Ltd.

Polyvinylpyrrolidone (PVP): polyvinylpyrrolidone K30, Wako Pure Chemical Industries, Ltd.; or Kollidon 30, Kollidon 90F, BASF Japan Ltd.

Poly(vinyl alcohol) (PVA): polyvinyl alcohol 2800, partially hydrolysed, Wako Pure Chemical Industries, Ltd.; or polyvinyl alcohol (partially hydrolysed), PE-05JPS, Japan VAM & POVAL Co., Ltd.

Hyaluronic acid sodium salt (HA): derived from microorganism, NACALAI TESQUE, INC.; or hyaluronic acid sodium salt of the Japanese pharmacopoeia, Kewpie Corporation, or Shiseido Co., Ltd.

Poly(ethylene glycol) 400 (PEG400): Macrogol400, NIKKO Pharmaceutical Co., Ltd

Poly(ethylene glycol) 4000 (PEG4000): Macrogol4000, NIKKO Pharmaceutical Co., Ltd.

Popidone iodine (PVP-I): Isodine mouth wash, Meiji Seika Pharma Co., Ltd.

Chitosan (Chitosan 10): Wako Pure Chemical Industries, Ltd.

Water-soluble chitosan (Water-soluble chitosan): Kyounokusuriya Co., Ltd.

(a) Preparation of PAA/PVP Film

Aqueous or ethanol solution of PAA (940 or 934) (0.5%, 100 μL) was cast onto the substrate of polystyrene, polypropylene, or polyethylene, and was dried at 75° C. to afford a PAA film. After drying, aqueous PVP (K30) solution (0.77%, 100 μL) was added dropwise to the surface of the PAA film, and was dried at 75° C. Mixing ratio was set to PAA:PVP =1:1 in the repeating unit mole ratio.

(b) Preparation of PAA/PVP/PVA Film (1)

Aqueous or ethanol solution of PAA (940 or 934) (0.5%, 100 μL) was cast onto the substrate of polystyrene, polypropylene, or polyethylene, and was dried at 75° C. After drying, the mixture of the aqueous PVP (K30) solution (0.77%, 100 μL) and aqueous PVA solution (3.06%, 1-100 μL) was added dropwise to the surface of the PAA film, and was dried at 75° C. Mixing ratio was set to PAA:PVP:PVA=1:1:0.1–10 in the repeating unit mole ratio.

(c) Preparation of PAA/PVP/PVA Film (2)

The mixture of the aqueous solution of PAA (940 or 934) (0.5%, 100 μL) and aqueous PVA solution (3.06%, 0.5-50 μL) was cast onto the substrate of polystyrene, polypropylene, or polyethylene, and was dried at 75° C. After drying, the mixture of the aqueous PVP (K30) solution (0.77%, 100 μL) and aqueous PVA solution (3.06%, 0.5-50 μL) was added dropwise to the surface of the PAA film, and was dried at 75° C. Mixing ratio was set to PAA:PVP:PVA=1:1:0.1–10 in the repeating unit mole ratio.

(d) Preparation of PAA/PVP/HA Sponge (1)

To the mixed solution of aqueous PAA (934) solution (0.05%, 1 mL) and aqueous HA solution (0.04%, 1 mL) was added PVP (K30) solution (0.077%, 1 mL)). It was frozen at −80° C., and then freeze-dried at room temperature to afford a sponge. Mixing ratio was set to PAA:PVP:HA=1:1:0.14 in the repeating unit mole ratio.

(e) Preparation of PAA/PVP/PVA Film (3)

The mixture of the ethanol solution of PAA (934P NF) (0.5%, 1 mL) and aqueous PVA solution (3.06%, 100 μL) was cast onto the substrate of polystyrene, polypropylene, or polyethylene, and was dried at 75° C. After drying, the mixture of the ethanol solution of PVP (Kollidone 30 or 90F) (7.7%, 100 μL) and aqueous PVA solution (3.06%, 100-400 μL) was added dropwise to the surface of the PAA/PVA film, and was dried at 75° C. Mixing ratio was set to PAA:PVP:PVA=1:1:2–5 in the repeating unit mole ratio.

(f) Preparation of PAA/PVP/HA Sponge (2)

To the mixed solution of aqueous PAA (934P NF) solution (0.05%, 1 mL) and aqueous HA solution (0.04%, 1-5 mL) was added PVP ((Kollidone 30 or 90F) solution (0.077%, 1 mL)). It was frozen at between −20° C. and −80° C., and then freeze-dried at room temperature to afford a sponge. Mixing ratio was set to PAA:PVP:HA=1:1:0.14–0.7 in the repeating unit mole ratio.

(g) Preparation of PAA/PVP//PVA/PEG Film

The mixture of the ethanol solution of PAA (934P NF) (0.5%, 1 mL) and aqueous PVA solution (3.06%, 100 μL) was cast onto the substrate of polystyrene, polypropylene, or polyethylene, and was dried at 75° C. to afford a PAA/PVA film. After drying, the mixture of the ethanol solution of PVP (Kollidone 30 or 90F) (7.7%, 100 μL), aqueous PVA solution (3.06%, 200 μL), and ethanol solution of PEG400 or PEG4000 (3.06%, 100-500 μL) was added dropwise to the surface of the PAA/PVA film, and was dried at 75° C. to afford a soft transparent film.

(h) Preparation of PAA/PVP/PVA Film Containing Chitosan

The mixture of the ethanol solution of PAA (934P NF) (0.5%, 1 mL) and aqueous PVA solution (3.06%, 100 μL) was cast onto the substrate of polystyrene, polypropylene, or polyethylene, and was dried at 75° C. to afford a PAA/PVA film. After drying, the mixture of the ethanol solution of PVP (Kollidone 30 or 90F) (7.7%, 100 μL) and aqueous PVA solution (3.06%, 300 μL) was added dropwise to the surface of the PAA/PVA film, and was dried at 75° C. Just before the mixture was dried up completely, powder of chitosan was added to the surface, and then the mixture was dried up completely.

(i) Preparation of PAA/PVP/PVA Film Containing Water-Soluble Chitosan

The mixture of the ethanol solution of PAA (934P NF) (0.5%, 1 mL) and aqueous PVA solution (3.06%, 100 μL) was cast onto the substrate of polystyrene, polypropylene, or polyethylene, and was dried at 75° C. to afford a PAA/PVA film. After drying, the mixture of the ethanol solution of PVP (Kollidone 30 or 90F) (7.7%, 100 μL), aqueous PVA solution (3.06%, 300 μL) and aqueous solution of water-soluble chitosan (1%, 100 μL) was added dropwise to the surface of the PAA/PVA film, and was dried at 75° C. to afford the PAA/PVP/PVA film containing water-soluble chitosan.

(j) Preparation of PAA/PVP/PVA/PEG Film Containing Water-Soluble Chitosan

The mixture of the ethanol solution of PAA (934P NF) (0.5%, 1 mL) and aqueous PVA solution (3.06%, 100 μL) was cast onto the substrate of polystyrene, polypropylene, or polyethylene, and was dried at 75° C. to afford a PAA/PVA film. After drying, the mixture of the ethanol solution of PVP (Kollidone 30 or 90F) (7.7%, 100 μL), aqueous PVA solution (3.06%, 200 μL), ethanol solution of PEG400 or PEG4000 (3.06%, 100 μL), and aqueous solution of water-soluble chitosan (1%, 100 μL) was added dropwise to the surface of the PAA/PVA film, and was dried at 75° C. to afford the flexible PAA/PVP/PVA/PEG film containing water-soluble chitosan.

(k) Preparation of Water-Soluble Chitosan/PAA/PVP/PVA Film (1)

The mixture of the ethanol solution of PAA (934P NF) (0.5%, 1 mL) and aqueous PVA solution (3.06%, 100 μL) was cast onto the substrate of polystyrene, polypropylene, or polyethylene, and was dried at 75° C. to afford a PAA/PVA film. After drying, the mixture of the ethanol solution of PVP (Kollidone 30 or 90F) (7.7%, 100 μL) and aqueous PVA solution (3.06%, 300 μL) was added to the surface of the PAA/PVP film and was dried at 75° C. After drying, solution of water-soluble chitosan (1% in 50% ethanol, 500 μL) was added dropwise to the PAA/PVP/PVA film, and was dried at 75° C. to afford the water-soluble chitosan/PAA/PVP/PVA film.

(l) Preparation of Water-Soluble Chitosan/PAA/PVP/PVA Film (2)

The mixture of the ethanol solution of PAA (934P NF) (0.5%, 1 mL) and aqueous PVA solution (3.06%, 100 μL) was cast onto the substrate of polystyrene, polypropylene, or polyethylene, and was dried at 75° C. to afford a PAA/PVA film. After drying, the mixture of the ethanol solution of PVP (Kollidone 30 or 90F) (7.7%, 100 μL) and aqueous PVA solution (3.06%, 300 μL) was added to the surface of PAA/PVP film, and was dried at 75° C. Separately, the solution of water-soluble chitosan (0.3% in 50% ethanol) was cast and dried up to a chitosan film. Both films were attached by small amount of water to afford the water-soluble chitosan/PAA/PVP/PVA film.

(m) Preparation of PAA/PVP/PVA Film Containing Iodine (1)

The mixture of the ethanol solution of PAA (934P NF) (0.5%, 1 mL) and aqueous PVA solution (3.06%, 100 μL) was cast onto the substrate of polystyrene, polypropylene, or polyethylene, and was dried at 75° C. to afford a PAA/PVA film. After drying, commercially available aqueous solution of PVP-I (100 μL), and aqueous PVA solution (3.06%, 300 μL) was added dropwise to the surface, and was dried at 75° C. to afford a film having antibacterial activity.

(n) Preparation of PAA/PVP/PVA Film Containing Iodine (2)

The mixture of the ethanol solution of PAA (934P NF) (0.5%, 1 mL) and aqueous PVA solution (3.06%, 100 μL) was cast onto the substrate of polystyrene, polypropylene, or polyethylene, and was dried at 75° C. to afford a PAA/PVA film. After drying, commercially available aqueous solution of PVP-I (10 μL), ethanol solution of PVP (Kollidone 30 or 90F) (7.7%, 90 μL) and aqueous PVA solution (3.06%, 300 μL) was added dropwise to the surface, and was dried at 75° C. to afford a film having antibacterial activity.

(o) Preparation of PAA/PVP/HA Sponge Containing Chitosan

To the mixed solution of aqueous PAA (934P NF) solution (0.05%, 1 mL) and aqueous HA solution (0.04%, 1 mL) was added PVP (Kollidon 30 or 90F) solution (0.077%, 1 mL) containing powder of chitosan 10 (5 mg). It was frozen at −20° C., and then freeze-dried at room temperature to afford a sponge. Mixing ratio was set to PAA:PVP:HA=1:1:0.14 in the repeating unit mole ratio.

(p) Preparation of PAA/PVP/HA Sponge Containing Water-Soluble Chitosan

The solution of aqueous PAA (934P NF) solution (0.05%, 1 mL), aqueous HA solution (0.04%, 1-3 mL), and aqueous solution of PVP (Kollidon 30 or 90F) (0.077%, 1 mL) were mixed. An aqueous solution of water-soluble chitosan (0.05%, 1 ml) was added to the mixture. It was frozen at −20° C., and then freeze-dried at room temperature to afford a sponge. Mixing ratio was set to PAA:PVP:HA=1:1:0.14–0.42 in the repeating unit mole ratio.

(q) Preparation of PAA/PVP/HA/PEG Powder

To the mixed solution of aqueous PAA (934P NF) solution (0.05%, 1 mL) and aqueous HA solution (0.04%, 1 mL) were added PVP (Kollidon 30 or 90F) solution (0.077%, 1 mL) and aqueous solution of PEG400 or PEG4000 (0.0306%-0.153%, 1 mL). It was frozen at −80° C., freeze-dried at room temperature, and then crashed by stirring to afford a powder of PAA/PVP/HA/PEG.

(r) Preparation of PAA/PVP Powder

Aqueous solution of PAA (934P NF) (0.05%) and aqueous solution of PVP (Kollidon 30) were mixed and simultaneously spray-dried by the spray-drier equipped with a four-stream nozzle (Fujisaki Electric Co., Ltd.) to afford PAA/PVP powder.

(s) Preparation of PAA/PVP/HA Papyraceous Sheet

The ethanol solution of PAA (934P NF) (0.5%, 1 mL) was cast onto the substrate of polystyrene, polypropylene, or polyethylene, and was dried at 75° C. After drying, the mixture of the aqueous solution of HA (0.4%, 0-1 mL) and aqueous solution of PVP (Kollidone 30 or 90F) (0.77%, 1 mL) was added dropwise to the surface of dried PAA film. It was frozen at −20° C., and then freeze-dried at room temperature to afford a papyraceous sheet. Mixing ratio was set to PAA:PVP:HA=1:1:0–0.14 in the repeating unit mole ratio.

(t) Preparation of PAA/PVP/HA Papyraceous Sheet Attached to Gauze

The ethanol solution of PAA (934P NF) (0.5%, 1 mL) was cast onto the substrate of polystyrene, polypropylene, or polyethylene, and was dried at 75° C. After drying, the mixture of the aqueous solution of HA (0.4%, 0-1 mL) and aqueous solution of PVP (Kollidone 30 or 90F) (0.77%, 1 mL) was added dropwise to the surface of dried PAA film. It was frozen at −20° C., and then gauze moistened by water was put on the upper surface or bottom surface. It was freeze-dried at room temperature to afford a papyraceous sheet attached to gauze. Mixing ratio was set to PAA:PVP:HA=1:1:0–0.14 in the repeating unit mole ratio.

(u) Preparation of Overlaid Film

Two to five films or papyraceous sheets mentioned above were bonded by a small amount of water or aqueous solutions of water-soluble polymers, and then dried to afford film or papyraceous sheets of the overlaid structure. By bonding with film of sodium alginate or agarose, or with gauze, the film having adhesive surface on one side was obtained.

(v) Preparation of Compressed PAA/PVP/HA Sponge Attached to Gauze

To the mixed solution of aqueous PAA (934P NF) solution (0.05%, 1 mL) and aqueous HA solution (0.04%, 0-5 mL) was added PVP (Kollidon 30 or 90F) solution (0.077%, 1 mL). It was added to the container of which the gauze was laid in the bottom. It was frozen at between −20° C. and −80° C., and then freeze-dried at room temperature. After freeze-drying, lightly compressing the freeze-dried product to afford a compressed PAA/PVP/HA sponge attached to gauze. Mixing ratio was set to PAA:PVP:HA=1:1:0.–0.7 in the repeating unit mole ratio.

Example 2: Evaluation of Adhesion Barrier Effect in the Adhesion-Model Mice

Mice (ddY, male, 6-8 weeks old) were anesthetized by injection of pentobarbital. The abdomen was incised and the cecum was exposed. It was burned with a heated spatula, and the film provided by the present invention (PAA:PVP:PVA=1:1:10 in the repeating unit mole ratio) was put on the burned site. The cecum was replaced in the cavity, and the abdomen was closed. After 3 days, or a week, abdomen was again incised under anesthesia, and the adhesion barrier effect was evaluated. As a result, in mice without treatment by the film, the cecum strongly adhered to other intestines or abdominal wall. On the other hand, in mice treated by the film, the film became a gel absorbing blood or lymph fluid around the burned site, and strongly adhered to the burned site, and adhesion to other intestines or abdominal wall was not observed. From these results, it was confirmed that the film provided by the present invention has a high adhesion barrier effect.

Example 3: Evaluation of Hemostatic Effect in Mice

Mice (ddY, male, 6-8 weeks old) were anesthetized by injection of pentobarbital. The abdomen was incised and incision was given on the liver. The film provided by the present invention (PAA:PVP:PVA=1:1:10 in the repeating unit mole ratio) was put on the incised site, and it was observed for one hour to evaluate the hemostatic effect. It was confirmed that the film being attached immediately became a gel absorbing blood, and strongly adhered to the incised site, and the hemostasis was achieved effectively.

Example 4: Evaluation of Hemostatic Effect in Mice

Mice (ddY, male, 6-8 weeks old) were anesthetized by injection of pentobarbital. The femoral vein was exposed, and cut, and the film provided by the present invention (PAA:PVP:PVA=1:1:10 in the repeating unit mole ratio), or the sponge provided by the present invention (PAA:PVP:HA=1:1:1.4 in the repeating unit mole ratio) was put on the incised site. It was observed for one hour to evaluate the hemostatic effect. As a result, the film or sponge immediately became a gel absorbing blood, and strongly adhered to the incised site, and the hemostasis was achieved effectively.

Example 5: Evaluation of Pressure Resistance for Hemostatic Effect

The bottoms of two cylindrical plastic tubes were connected with a rubber tube. After having filled the inside with water or color water, chicken skin was bound to the upper part of one tube, and a hole was made in the chicken skin with a needle of 21G. The film provided by the present invention (PAA:PVP:HA=1:1:1.4 in the repeating unit mole ratio) was put on the hole, and made it adhere to the skin. The position of the tubes was moved lengthwise to make the film be subjected to hydraulic pressure, and observed a leak of the water. The film immediately absorbs water, and strongly adhered to the chicken skin, and completely restrained the leak of the water up to hydraulic pressure of 30 mmHg.

Example 6: Evaluation of Hemostatic Effect in Heparinized Mice

Mice (ddY, male, 6-8 weeks old) were anesthetized by injection of pentobarbital. The femoral vein was exposed, and cut, and the films provided by the present invention mentioned in (a)-(c), (e), (g)-(n), or (u), or the sponges provided by the present invention mentioned in (d), (f), (o), (p), (s), or (t), or the powder provided by the present invention mentioned in (q), or (r), or the mixture of the powder provided by the present invention mentioned in (q), or (r) and the powder of chitosan 10, was put on the incised site. It was observed for one hour to evaluate the hemostatic effect. As a result, the film or sponge or powder immediately became a gel absorbing blood, and strongly adhered to the incised site, and the hemostasis was achieved effectively. Especially, in the films, sponges, and powder containing chitosan, the hemostatic effect was greatly improved.

Example 7: Evaluation of Hemostatic Effect in Clinical Study (1)

The film provided by the present invention mentioned in (c) was put on the needle puncture site of the patients taking warfarin. The film became a gel, and adhered to the puncture site, and speedy hemostasis was achieved.

Example 8: Evaluation of Hemostatic Effect in Clinical Study (2)

After tooth extraction, the sponge provided by the present invention mentioned in (d) was put in the socket in the patients taking warfarin. The sponge became a gel, and adhered to the applied position, and speedy hemostasis was achieved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A method for producing a dried film including poly (acrylic acid) and polyvinylpyrrolidone, the method comprising:
   preparing a film-state material in a dried state from either a solution of poly(acrylic acid) or a solution of polyvinylpyrrolidone; and
   bringing the film-state material into contact with the other remaining solution, followed by being dried,
   wherein the dried film forms a hydrogel having adhesiveness to a bio-tissue when the dried film absorbs water or blood.

2. The method according to claim 1, the method comprising:
   preparing the film-state material in the dried state from the solution of poly(acrylic acid); and
   bringing the film-state material into contact with the solution of polyvinylpyrrolidone, followed by being dried.

3. The method according to claim 1, wherein one of or both of the solutions of poly(acrylic acid) and polyvinylpyrrolidone include(s) a water-soluble polymer.

4. The method according to claim 3, wherein the water-soluble polymer is poly(vinyl alcohol).

5. The method according to claim 3, wherein the water-soluble polymer is polyethylene glycol.

6. The method according to claim 1, wherein a repeating unit molar ratio of either poly(acrylic acid) or polyvinylpyrrolidone included in the film-state material to poly(acrylic acid) or polyvinylpyrrolidone in the other remaining solution to be used for contacting is at the range of 0.1 or more to 10 or less.

7. The method according to claim 1, wherein the dried film is a medical treatment material or a component thereof.

8. The method according to claim 7, wherein the medical treatment material is an adhesion barrier or a hemostatic device.

9. The method according to claim 7, wherein the medical treatment material is a wound covering material.

* * * * *